(12) United States Patent
Hawthorne et al.

(10) Patent No.: US 6,323,372 B1
(45) Date of Patent: Nov. 27, 2001

(54) SYNTHESIS OF PERHYDROXYDODECABORATE SALTS AND RELATED SPECIES

(75) Inventors: M. Frederick Hawthorne, Encino; Toralf Peymann; Axel Hans-Joachim Herzog, both of Los Angeles, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/546,108

(22) Filed: Apr. 10, 2000

(51) Int. Cl.$^7$ .................................................. C07F 5/02
(52) U.S. Cl. ........................................ 568/5; 568/4
(58) Field of Search ................................... 568/4, 5

(56) References Cited

U.S. PATENT DOCUMENTS

| | | |
|---|---|---|
| 3,390,966 | 7/1968 | Knoth, Jr. ............................. 23/361 |
| 3,551,120 | 12/1970 | Millet et al. ......................... 23/358 |

OTHER PUBLICATIONS

CA:131:19038 abs of Angew. Chem. Int. Ed. 38(8) pp 1062–1064 by Peymann et al, 1999.*
CA:77:126475 abs of Recl. Trav. Chim. Pays–Bas by Elferink et al 91(8) pp 989–1001, 1972.*

Kenneth Shelly, Carolyn B. Knobler, and M. Frederick Hawthorne, *Synthesis of Monosubstituted derivatives of Closo–Decahydrodecabonate (2–) . X–Ray Crystal Structures of [Closo–2–B10H9NCO]2–*, Inorganic Chemistry, vol. 31 No. 13, 1992. pp. 28892892.

M. Frederick Hawthorne, Richard L. Pilling, and Philip M. Garrett, *A Study of the Reaction of Hydroxide Ion With B20H18–2*, Journal of the American Chemical Society 87: Nov. 21, 1965, pp. 4740–4745.

* cited by examiner

*Primary Examiner*—Jean F. Vollano
(74) *Attorney, Agent, or Firm*—Koppel & Jacobs; Michael J. Ram

(57) ABSTRACT

New icosahedral borohydrates $Cs_2[closo-B_{12}(OH)_{12}]$; $Cs[closo-1-H-1-CB_{11}(OH)_{11}]$; and $closo-1,12-H_2-1,12-C_2B_{10}(OH)_{10}$ are disclosed. Also set forth are their preparation by refluxing the icosahedral boranes $[closo-B_{12}H_{12}]^{2-}$, $[closo-1-CB_{11}H_{12}]^-$ and $closo-1,12-(CH_2OH)_2-1,12-C_2B_{10}H_{10}$ with a hydroxylating agent, preferably $30\%_w$ hydrogen peroxide.

11 Claims, 3 Drawing Sheets

SYNTHESIS OF PERHYDROXYDODECABORATE SALTS AND RELATED SPECIES

This invention was made with Government support under Contract No. DE-FG02-92ER61975 awarded by the Department of Energy. The Government has certain rights in this invention.

The present invention relates to unique three-dimensional hydoxylated icosahedral boron cage compounds.

BACKGROUND

Scientists have formed numerous different polyhydroxylated molecules. Carbon-based systems are well-known. For example, carbohydrates are ubiquitous in nature and serve as a source for chemical energy (glucose), the backbone for genetic information (ribose), and the organic constituents of plants (cellulose) or insects (chitin) (D. Voet, J. G. Voet, *Biochemistry*, 2nd ed., Wiley, N.Y., 1995, pp. 251–276. The three-dimensional network of silica and its derived minerals (F. Liebau, *Structural Chemistry of Silicates*, Springer, N.Y., 1985, p. 4) results from the condensation of polyhydroxylated silicates.

However, very few polyhydroxylated boron compounds are known. The most prominent polyhydroxylated boron compound is boric acid, $B(OH)_3$. Alkaline solutions of $B(OH)_3$ deposit $Na_2[B_4O_5(OH)_4] \cdot nH_2O$, which constitutes two abundant boron minerals, kernite (n=2) and borax (n=8) (F. A. Cotton, G. Wilkinson, *Advanced Inorganic Chemistry*, 5th ed., Wiley, N.Y., 1988, pp. 164–169.). Other common boron structures include the trigonal and tetrahedral boron-oxygen units common to borate minerals, (G. A. Heller, *Top. Curr. Chem.* 1986, 131, 39–98), and the icosahedron. The allotropes of elemental boron, (J. Donohue, *The Structures of the Elements*, Wiley, N.Y., 1974, pp. 48–82) boron-rich solids (H. Hubert, B. Devouard, L. A. J. Garvie, M. O'Keeffe, P. R. Buseck, W. T. Petuskey, P. F. McMillan, *Nature* 1998, 391, 376–378) and the parent anion of the polyhedral boranes, $[closo-B_{12}H_{12}]^{2-}$ First reported by Hawthorne et al (A. R. Pitochalli and M. F. Hawthorne *J. Am.Chem. Soc.*, 1960, 82, 3228 followed by J. A. Wunderlich, W. N. Lipscomb, *J. Am. Chem. Soc.* 1960, 82, 4427–4428) all contain $B_{12}$ icosahedral The charge-delocalized icosahedral ion $[closo-B_{12}H_{12}]^{2-}$, may be considered as the parent aromatic species for borane chemistry in a manner similar to that served by the benzene ring in organic (carbon) chemistry (M. F. Hawthorne, *Advances in Boron Chemistry*, Special Publication No. 201, Royal Society of Chemistry, London, 1997, pp. 261–272). However, while certain benzene and other aromatic compounds are known,(ie., phenol, hydroquinone, naphthol) fully hydroxylated aromatic compounds (all —H replaced by —OH) are not known or readily prepared. However, contrary to the process described herein for manufacturing the new hydoxylated borates, no reaction occurs when benzene is refluxed with boiling hydrogen peroxide. Isoelectronic substitution of one or two: B—H vertices in $[closo-B_{12}H_{12}]^2$ by: C—H$^+$ provides the aromatic derivatives $[closo-1-CB_{11}H_{12}]^-$, and a set of three isomeric dicarbacarboranes (1,2- or ortho; 1,7- or meta; and 1,12- or para) $closo-C_2B_{10}H_{12}$ R (N. Grimes, *Carboranes*, Academic Press, New York, 1970, p. 8). Each of these isoelectronic derivatives of $[closo-B_{12}H_{12}]^{2-}$, undergoes characteristic hydrogen-substitution reactions at their B—H vertices resulting in a huge number of known icosahedral species. Of special interest are derivatives in which every available B—H vertex has been substituted. Thus, hydrophobic derivatives of $[closo-B_{12}H_{12}]^2$ and $[closo-1-CB_{11}H_{12}]^-$, and the three isomeric dicarboboranes, such as $[closo-B_{12}Cl_{12}]^{2-}$ (W. H. Knoth, H. C. Miller, J. C. Sauer, J. H. Balthis, Y. T. Chia, E. L. Muetterties, *Inorg, Chem,* 1964, 3, 159–167), $[closo-CB_{11}(CH_3)_{12}]^-$, (King, B. T.; Janousek, Z.; Grüner, B.; Trammell, M.; Noll, B. C.; Michl, J. *J. Am. Chem. Soc.* 1996, 118, 10902–10903), $closo-1,12-C_2B_{10}(CH_3)_{12}$, (W. Jiang, C. B. Knobler, M. D. Mortimer, M. F. Hawthorne, *Angew. Chem.* 1995, 107, 1470–1473; *Angew. Chem. Int. Ed. Engl.* 1995, 34, 1332–1334.) and, $[closo-B_{12}(CH_3)_{12}]^{2-}$ (T. Peymann, C. B. Knobler, M. F. Hawthorne, *J.Am. Chem. Soc.*, 1999, 121, 5601) have been synthesized. However, the existence or formulation of similar highly substituted polyhedral borane derivatives having hydrophilic substituents, such as hydroxyl have not been demonstrated.

SUMMARY

It has now been found that per-B-hydroxylated icosahedral borane derivatives, which may be considered to be derivatives of a new type of polyhedral sub-boric acid, can be readily synthesized. Described herein are the per-B-hydroxylated icosahedral $Cs_2[closo-B_{12}(OH)_{12}]$; $Cs[closo-1-H-1-CB_{11}(OH)_{11}]$; and $closo-1,12-H_2-1,12-C_2B_{10}(OH)_{10}$. These new borohydrate compounds are prepared by the oxidation of the icosahedral boranes $[closo-B_{12}H_{12}]^{2-}$, $[closo-1-CB_{11}H_{12}]^-$ and $closo-1,12-CH_2OH)_2-1,12-C_2B_{10}H_{10}$, respectively, with 30%$_w$ hydrogen peroxide at the reflux temperature (from about 100° C. to 50° C.)

BRIEF DESCRIPTION OF DRAWINGS

These and other features, aspects and advantages of the present invention will become better understood with reference to the following description, appended claims, and accompanying drawings, where:

DETAILED DESCRIPTION $Cs_2[closo-B_{12}(OH)_{12}]$, $Cs[closo-1-H-1-CB_{11}(OH)_{11}]$, and $closo-1,12-H_2-1,12-C_2B_{10}(OH)_{10}$ are prepared by refluxing between 100° C. and 150° C., the icosahedral boranes $[closo-B_{12}H_{12}]^{2-}$, $[closo-1-CB_{11}H_{12}]^-$ and $closo-1,12-(CH_2OH)_2-1,12-C_2B_{10}H_{10}$, respectively, as shown in FIGS. 3–5, with 30% (by volume) hydrogen peroxide. While 30% (by weight, %$_w$) hydrogen peroxide boils at 222° F. (106° C.) and 100% hydrogen peroxide boils at about 150° C., the reflux temperature in the reactions will depend on the specific boron compound utilized, its concentration in the reaction mixture and the extent of reaction. As shown in FIGS. 3–5, the borane was refluxed for 4 days and the carboranes were refluxed for 15 hours.

Figure 1:
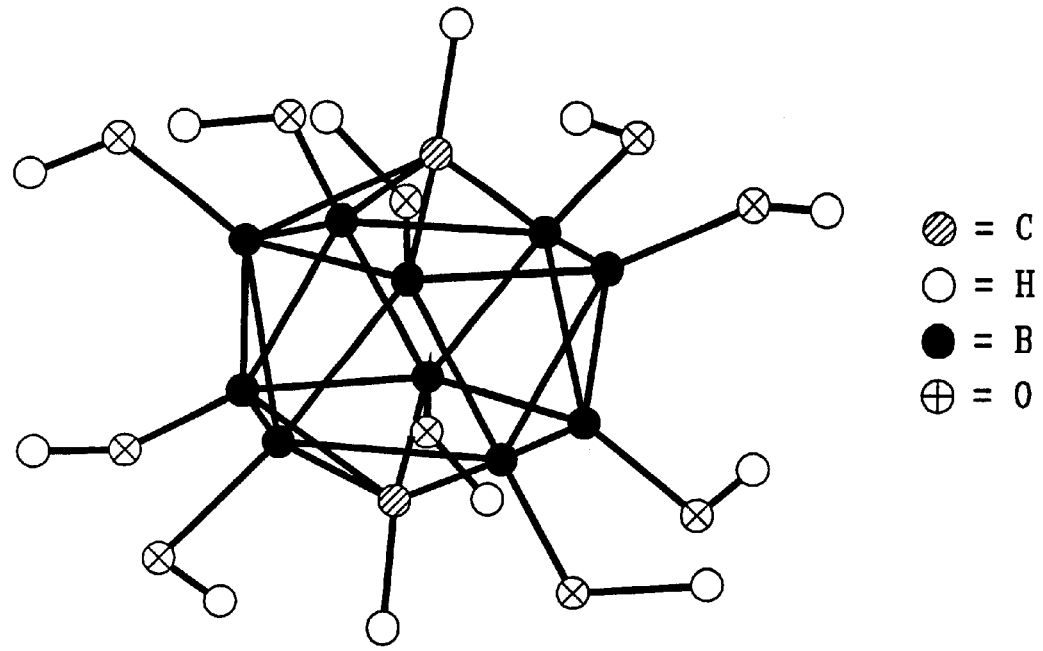
FIG. 1 is an ORTEP diagram of $closo-1,12-H_2-1,12-C_2B_{10}(OH)_{10}$.
Figure 2:
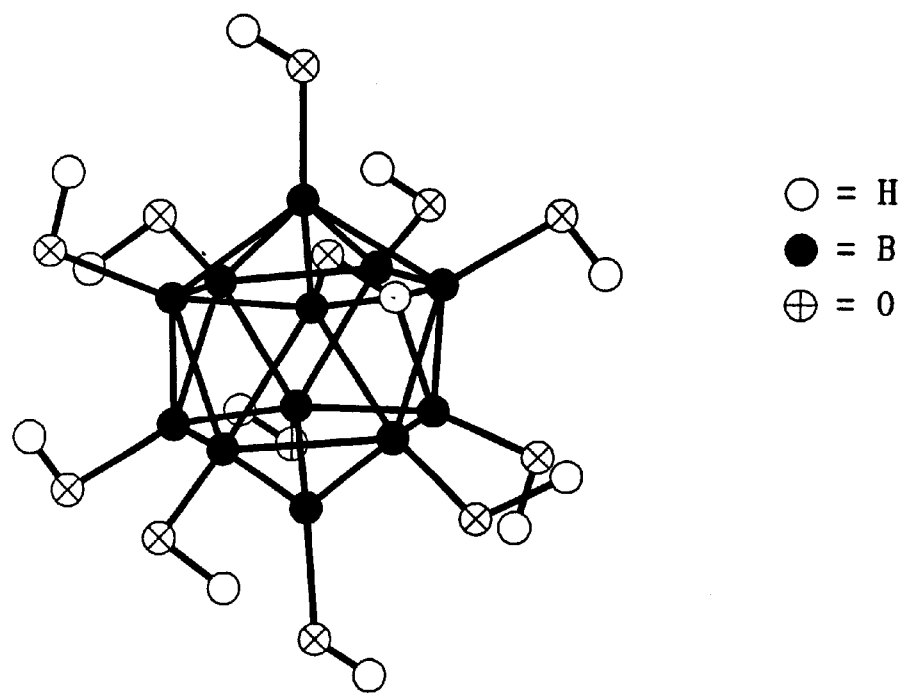
FIG. 2 is an ORTEP diagram of $Cs_2[closo-B_{12}(OH)_{12}]$.

$Cs_2[closo-B_{12}(OH)_{12}]$ is shown in FIG. 1 and $closo-1,12-H_2-1,12-C_2B_{10}(OH)_{10}$ is shown in FIG. 2. These new compounds were characterized by $^{11}B$ NMR spectroscopy, electrospray mass spectrometry, and single-crystal X-ray diffraction of $Cs_2[closo-B_{12}(OH)_{12}]$ and $closo-1,12-H_2-1,12-C_2B_{10}(OH)_{10}$.

The $^{11}$B NMR spectra of these three new compounds are consistent with their structures in that $Cs_2[closo-B_{12}(OH)_{12}]$ (point group $I_h$) gave a singlet at −17.1 ppm; $Cs[closo-1-H-1-CB_{11}(OH)_{11}]$, ($C_{5v}$) exhibited three singlets at −7.3, −15.5, and −17.1 ppm; and closo-1,12-$H_2$-1,12-$C_2B_{10}(OH)_{10}$ ($D_{5d}$) displayed a singlet at −17.0 ppm. Electrospray mass spectrometry confirmed the m/z values expected for the assigned polyhydroxylated structures $Cs_2[closo-B_{12}(OH)_{12}]$, and $Cs[closo-1-H-1-CB_{11}(OH)_{11}]$. The sparingly water-soluble salts $Cs_2[closo-B_{12}H_{12}]^{2-}$ and $Cs[closo-1-CB_{11}H_{12}]^-$, served as precursors for $Cs_2[closo-B_{12}(OH)_{12}]$ and $Cs[closo-1-H-1-CB_{11}(OH)_{11}]$, respectively. The synthesis of closo-1,12-$H_2$-1,12-$C_2B_{10}(OH)_{10}$ employed the slightly water-soluble precursor closo-1,12-$CH_2OH)_2$-1,12-$C_2B_{10}H_{10}$, because closo-1,12-$C_2B_{10}H_{12}$ is not water-soluble and hence not available to the hydrogen peroxide reagent. During this reaction sequence, the diol closo-1,12-$(CH_2OH)_2$-1,12-$C_2B_{10}H_{10}$, is most likely oxidized to the corresponding dicarboxylic acid, which subsequently decarboxylates during B-hydroxylation to afford species closo-1,12-$H_2$-1,12-$C_2B_{10}(OH)_{10}$.

Figure 3:
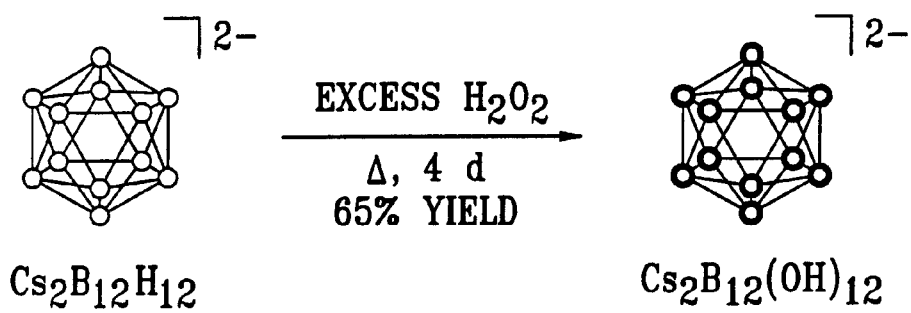
FIG. 3 shows the reaction scheme for formation of $Cs_2[closo-B_{12}(OH)_{12}]$.
Figure 4:
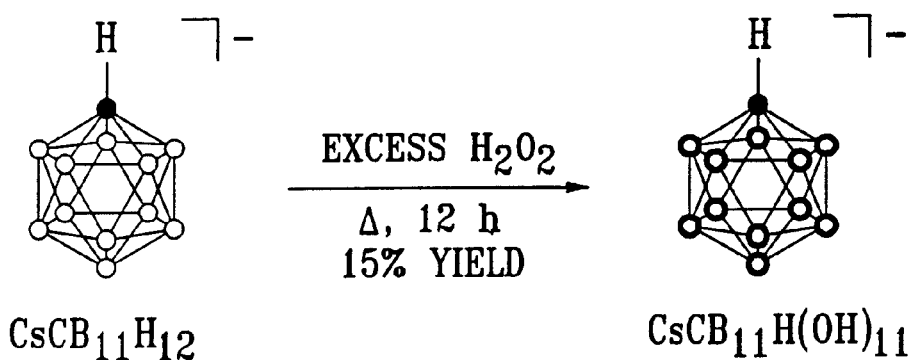
FIG. 4 shows the reaction scheme for formation of $Cs[closo-1-H-1-CB_{11}(OH)_{11}]$.
Figure 5:
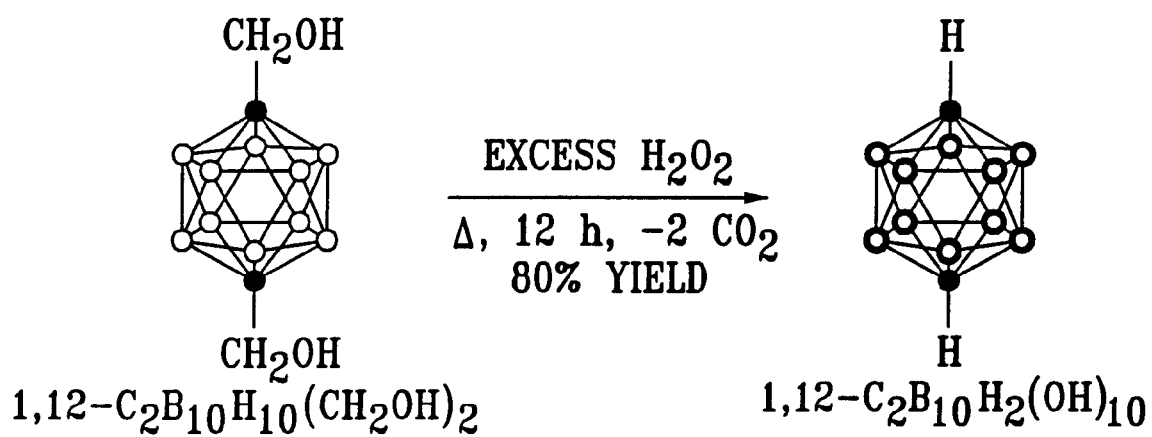
FIG. 5 shows the reaction scheme for formation of $closo-1,12-H_2-1,12-C_2B_{10}(OH)_{10}$.

Because the per-B-hydroxylated species are thermodynamically unstable with respect to boric acid, it would be expected that, continued reaction with $H_2O_2$ would lead to degradation of this product under experimental conditions. Unexpectedly, it was found that the yields from the syntheses shown in FIGS. 3–5 are 80% for closo-1,12-$H_2$-1,12-$C_2B_{10}(OH)_{10}$, 65% for $Cs_2[closo-B_{12}(OH)_{12}]$ and 31% for $Cs[closo-1-H-1-CB_{11}(OH)_{11}]$. This distribution reflects the higher kinetic stabilities of the two centrosymmetric cage structures of $[closo-B_{12}H_{12}]^{2-}$ and closo-1,12-$C_2B_{10}H_{10}$ relative to that of the polarized cluster $[closo-1-CB_{11}H_{12}]^-$.

One unexpected feature of the anion present in $Cs_2[closo-B_{12}(OH)_{12}]$ is the low solubility of its alkali-metal salts in water even though its surface is covered with hydroxyl groups. Thus, $Cs_2[closo-B_{12}(OH)_{12}]$ can be recrystallized from water, whereas the $Li_2$, $Na_2$, and $K_2$ salts of $Cs_2[closo-B_{12}(OH)_{12}]$ precipitate quantitatively upon addition of the corresponding alkali-metal chloride to warm aqueous solutions of $Cs_2[closo-B_{12}(OH)_{12}]$. The dicesium salt is freely soluble in water since cesium is to large to effectively coordinate to the $[B_{12}(OH)_{12}]^{2-}$ ion. While $[B_{12}(OH)_{12}]^{2-}$ may be viewed as an intermediate in the hydrolylation reaction, the anion present in $Cs_2[closo-B_{12}(OH)_{12}]$ probably functions as a strong multihapto ligand with the smaller alkali-metal ions displacing their water of hydration, crosslinking, and precipitating the aggregated alkali-metal salts. Closo-1,12-$H_2$-1,12-$C_2B_{10}(OH)_{10}$, is insoluble in water as well as in organic solvents; this can be attributed to the absence of a dipole moment and the strong network of the hydrogen bonding between its pendant hydroxyl groups in the crystal lattice. The closeness of this network is reflected by the density of the compound (1.73 g cm$^{-3}$), which is unusually high for a covalent organic compound. For comparison, the density of closo-1,12-$H_2$-1,12-$C_2B_{10}(CH_3)_{10}$ is 0.97 g cm$^{-3}$ (W. Jiang, C. B. Knobler, M. D. Mortimer, M. F. Hawthorne, *Angew. Chem.* 1995, 107, 1470–1473; *Angew. Chem. Int. Ed. Engl.* 1995, 34, 1332–1334.). The overall geometry of the icosahedral framework in both $Cs_2[closo-B_{12}(OH)_{12}]$ and closo-1,12-$H_2$-1,12-$C_2B_{10}(OH)_{10}$, is not affected by per-B-hydroxylation.

In the solid state monoclinic structure of closo-1,12-$H_2$-1,12-$C_2B_{10}(OH)_{10}$ shown in FIG. 1, space group C2/c; a=15.960(13) Å, b=7.812(6) Å, c=11.867(10) Å, β=118.28 (2)°, V=1303 Å, ρ=1.73 g cm$^{-3}$, $2\theta_{max}$=60°, $\lambda(Mo_{K\alpha})$=0.71069 Å, θ-2θ scan mode, 298° K. Of the 1902 unique reflections measured, 1013 were considered observed, [I>2σ (I)]. Data were corrected for Lorentz and polarization effects but not for absorption, $\mu$=1.5 cm$^{-1}$. Atoms were located by use of statistical methods (SHELX86). 115 parameters were refined. Water hydrogen atoms were included as located. All other hydrogen atoms were included in calculated positions after they had been located. R=0.067, wR=0.193 refined against $|F^2|$. Further details of the X-ray structure determination may be obtained from the Fachinformationszentrum Karlsruhe, D-76344 Eggenstein-Leopoldshafen (Germany), on quoting the depository number CSD-410414. The B—B [177.6(5)–183.7(5) pm] and the B—C [171.6(5)–173.4(5) pm] bond distances are similar to those of unsubstituted closo-1,12-$C_2B_{10}H_{12}$ determined by electron diffraction [B—B=177.2(13)–179.2(7) pm, B—C=171.0(11) pm] (R. K. Bohn, M. D. Bohn, *Inorg. Chem.* 1971, 10, 350–355).

Similarly, in monoclinic $Cs_2[closo-B_{12}(OH)_{12}]\cdot 2H_2O$, space group $P2_1/a$, a=13.135(9) Å, b=7.342(6) Å, c=8.304 (6) Å, β=97.39(2)°, V=794 Å, ρ=2.66 g cm$^{-3}$, $2\theta_{max}$=115°, $\lambda(Cu_{K\alpha})$=1.5418 Å, θ-2θ scan mode, 298 K°. Of the 1079 unique reflections measured, 1015 were considered observed, [I>2σ(I)]. Data were corrected for Lorentz and polarization effects and for absorbtion, $\mu$=3.6 cm$^{-1}$. Atoms were located by use of statistical methods (SHELXS90). 98 parameters were refined. Water hydrogen atoms were not located. All other hydrogen atoms were included as located. R=0.045, wR=0.124, refined against $|F^2|$. Further details of the X-ray structure determination may be obtained from the Fachinformationszentrum Karlsruhe,D-76344 Eggenstein-Leopoldshafen (Germany), on quoting the depository number CSD-410413. (R. K. Bohn, M. D. Bohn, *Inorg. Chem.* 1971, 10, 350–355). The B—B distances of anion shown in FIG. 2 (177.5(9)–181.4(9) pm) do not deviate significantly from those present in $[closo-B_{12}H_{12}]^{2-}$, (175.5(7)–178.0(7) pm (J. A. Wunderlich, W. N. Lipscomb, *J. Am. Chem. Soc.* 1960, 82, 4427–4428). The B—O bond lengths of the $Cs_2[closo-B_{12}(OH)_{12}]$ anion are elongated by about 5 pm compared with closo-1,12-$H_2$-1,12-$C_2B_{10}(OH)_{10}$ (143.3(7) –145.9(9) pm compared to 138.6(4)–140.3(4) pm), which may be due to the interaction of the delocalized negative charge in $Cs_2[closo-B_{12}(OH)_{12}]$ and the B—O dipoles.

The only other derivative of $[closo-B_{12}H_{12}]^{2-}$ that is saturated with twelve chalcogen substituents is the selenoborate $Cs_8[closo-B_{12}(Se_2BSe)_6]$ obtained directly from elemental boron, $Cs_2Se$, and selenium at 700° C. in a sealed glass ampoule (J. Küper, O. Conrad, B. Krebs, *Angew. Chem.* 1997, 109, 1995–1996; *Angew. Chem. Int. Ed. Engl.* 1997, 36, 1903–1904). The structure of this species displays —Se—B(Se)—Se— bridges between neighboring boron vertices of the icosahedron. Related species, in which two or three neighboring B—O vertices are bridged by a trigonal or tetrahedral boron atom appear to be likely targets for synthesis. For example, $(Cs_2[closo-B_{12}(O_2BOH)_6]$, $Cs_2[closo-B_{12}(O_3Si\ CH_3)_4]$ and $Cs_2[closo-B_{12}(O_3CCH_3)_4]$ are likely candidates.

The ability to produce $Cs_2[closo-B_{12}(OH)_{12}]$, $Cs[closo-1-H-1-CB_{11}(OH)_{11}]$ and closo-1,12-$H_2$-1,12-$C_2B_{10}(OH)_{10}$, opens up a new field of boron cluster chemistry, wherein the aromatic icosahedral cluster functions as the scaffolding for reactions that would be performed on its oxygen sheathing. Fox example, $Cs_2[closo-B_{12}(OH)_{12}]$ can be used as the central core for the formation of multioligomeric organic and inorganic compounds similar to dendrimers (G. R. Newkome, C. N. Moorefield, F. Vögtle, *Dendritic Molecules*, VCH, New York, 1996). except that the oligomeric chains will emanate from a molecular surface rather than a single atoms. Furthermore, it is believed that the high temperature pyrolysis of a simple salt of $Cs_2[closo\text{-}B_{12}(OH)_{12}]$, might form a polymeric network of very stable icosahedral connected by covalent B—O—B bonds. Species of this sort are expected to be chemically inert and very hard due to strong B—O bonds. However, the polymeric array of dianionic cages is expected to serve as a source of electrons for chemical processes while still retaining water solubility. In addition, the possibilities of the covalent incorporation of species, such as $Cs_2[closo\text{-}B_{12}(OH)_{12}]$, in metal oxide lattices are boundless.

In the following examples the $^{11}B$ NMR spectra were obtained with a Bruker AM-500 spectrometer at 160 MHz. $^{11}B$ NMR chemical shifts were externally referenced to $BF_3.Et_2O$; peaks upfield of the reference are designated as negative. ESI mass spectra were recorded by injecting the sample dissolved in water into an ionspray source. The mass spectrometer was operated in the negative-ion mode.

Preparation of $Cs_2[closo\text{-}B_{12}(OH)_{12}$(FIG. 3)

A suspension of $Cs_2[closo\text{-}B_{12}H_{12}]$ (1.00 g, 2.5 mmol) was refluxed in 40 ml of 30% hydrogen peroxide for three–four days. The resultant solution was cooled overnight in a refrigerator to precipitate crude $Cs_2[closo\text{-}B_{12}(OH)_{12}]$. The precipitate was then recrystallized from water, collected by filtration and dried to provide 0.97 g (a 65% yield) of pure $Cs_2[closo\text{-}B_{12}(OH)_{12}]$, as a white powder. $^{11}B$ NMR ($H_2O$)): $\delta = -17.1$ (s); ESI-MS:m/z: 335.1 $\{[H][B_{12}(OH)_{12}]\}^-$.

Preparation of $Cs[closo\text{-}1\text{-}H\text{-}1\text{-}CB_{11}(OH)_{11}]$ (FIG. 4)

A suspension of $Cs[closo\text{-}1\text{-}CB_{11}H_{12}]$ (0.10 g, 0.36 mmol) was refluxed in 10 ml of 30% hydrogen peroxide for five hours. The resultant solution was cooled overnight in a refrigerator to precipitate crude $Cs[closo\text{-}1\text{-}H\text{-}1\text{-}CB_{11}(OH)_{11}]$, which was recrystallized from water. The product was collected by filtration and dried to provide a 31% yield of $Cs[closo\text{-}1\text{-}H\text{-}1\text{-}CB_{11}(OH)_{11}]$ as a white powder. $^{11}B$ NMR ($H_2O$): $\delta = -7.3$ (s, B12), $-15.3$ (s, B2-6), $-17.1$ (s, B7-11); ESI-MS:m/z: $319.0[HCB_{11}(OH)_{11}]^-$.

Preparation of $closo\text{-}1,12\text{-}H_2\text{-}1,12\text{-}C_2B_{10}(OH)_{10}$ (FIG. 5)

A suspension of $closo\text{-}1,12\text{-}(CH_2OH)_2\text{-}1,12\text{-}C_2B_{10}H_{10}$, (1.00 g, 4.90 mmol) was refluxed for 12 hours in 75 ml of 30% hydrogen peroxide. The colorless precipitate formed was filtered off and washed with water. After drying at 150° C. in a vacuum ($5\times10^{-5}$ mm), 1.19 g of pure $closo\text{-}1,12\text{-}H_2\text{-}1,12\text{-}C_2B_{10}(OH)_{10}$, was obtained giving an 80% yield, as a white powder. $^{11}B$ NMR ($H_2O$): $\delta = -17.0$.

It is evident from the foregoing that there are many additional embodiments of the present invention which, while not expressly described herein, are within the scope of this invention and may suggest themselves to one of ordinary skill in the art. For example, the invention contemplates that the concentration of the hydrogen peroxide can be varied, which will in turn effect the reflux temperature and may, in turn effect the reaction rate, time to completion of the reaction, and purity of the resultant boron compounds. Alternative reactants can also be used in place of the hydrogen peroxide. For example, peracids, such as metachloro perbenzoic acid using acetonitrile as a solvent or amine oxides, such as pyridine N-oxide, should be suitable replacements for the hydrogen peroxide. Also, inert diluents can be added to the reaction mixture to modify the reflux temperature without negatively modifying the desired end result. It is therefore intended that the invention be limited solely by the appended claims.

We claim:
1. $Cs[closo\text{-}1\text{-}H\text{-}1\text{-}CB_{11}(OH)_{11}]$.
2. $closo\text{-}1,12\text{-}H_2\text{-}1,12\text{-}C_2B_{10}(OH)_{10}$.
3. $[closo\text{-}1\text{-}H\text{-}1\text{-}CB_{11}(OH)_{11}]^-$.
4. A method of preparing three-dimensional hydoxylated icosahedral boron cage compounds containing at least 10 boron atoms, each boron atom having a hydroxyl group attached thereto, comprising:

refluxing three-dimensional icosahedral boron cage compounds containing at least 10 boron atoms, each boron atom having a hydrogen group attached there to, in a solution of a reactive hydroxylating agent.

5. The method of claim 4 wherein the three-dimensional icosahedral boron cage compounds are selected from the group consisting of $[closo\text{-}B_{12}H_{12}]^{2-}$, $[closo\text{-}1\text{-}CB_{11}H_{12}]^-$ and $closo\text{-}1,12\text{-}(CH_2OH)_2\text{-}1,12\text{-}C_2B_{10}H_{10}$.

6. The method of claim 4 wherein the three-dimensional hydoxylated icosahedral boron cage compound is $Cs_2[closo\text{-}B_{12}(OH)_{12}]$, $Cs[closo\text{-}1\text{-}H\text{-}1\text{-}CB_{11}(OH)_{11}]$, or $closo\text{-}1,12\text{-}H_2\text{-}1,12\text{-}C_2B_{10}(OH)_{10}$.

7. The method of claim 4 where the refluxing is conducted for from about 12 hours to about 4 days.

8. The method of claim 4 wherein the hydroxylating agent is a hydrogen peroxide.

9. The method of claim 8 wherein the hydrogen peroxide is a 30% by weight of hydrogen peroxide solution.

10. The method of claim 4 wherein the hydroxylating agent is a peracid or an amine oxide.

11. The method of claim 4 wherein the hydroxylating agent is metachloro perbenzoic acid or pyridine N-oxide.

* * * * *